United States Patent
Rezai et al.

(12) 
(10) Patent No.: US 6,438,423 B1
(45) Date of Patent: Aug. 20, 2002

(54) METHOD OF TREATING COMPLEX REGIONAL PAIN SYNDROMES BY ELECTRICAL STIMULATION OF THE SYMPATHETIC NERVE CHAIN

(75) Inventors: Ali R. Rezai; Martin Zonenshayn, both of New York City, NY (US)

(73) Assignee: ElectroCore Technique, LLC, Summit, NJ (US)

( * ) Notice: Subject to any disclaimer, the term of this patent is extended or adjusted under 35 U.S.C. 154(b) by 0 days.

(21) Appl. No.: 09/490,617

(22) Filed: Jan. 25, 2000

(51) Int. Cl.[7] .................................................. A61N 1/32

(52) U.S. Cl. ....................................................... 607/46

(58) Field of Search ........................ 607/43, 46, 68–75; 128/898

(56) References Cited

U.S. PATENT DOCUMENTS 5,995,873 A  * 11/1999 Rhodes

* cited by examiner

Primary Examiner—Jeffrey R. Jastrzab
(74) Attorney, Agent, or Firm—Joseph P. Errico; Timothy J. Bortree

(57) ABSTRACT

A method for treating complex regional pain syndromes by applying an oscillating electric field to appropriate sympathetic ganglia. The method includes the steps of inserting an electrode into the vicinity of the sympathetic ganglion, for example the stellate and upper thoracic ganglia, such that the necessary electric field may be applied to the ganglion. The necessary field oscillation frequency and strength, as well as other characteristics of the signal are determined individually for each patient. Continued driving of the pathological activity of the ganglion into the normal function is the long-term, reversible palatative remedy for the condition.

11 Claims, 2 Drawing Sheets

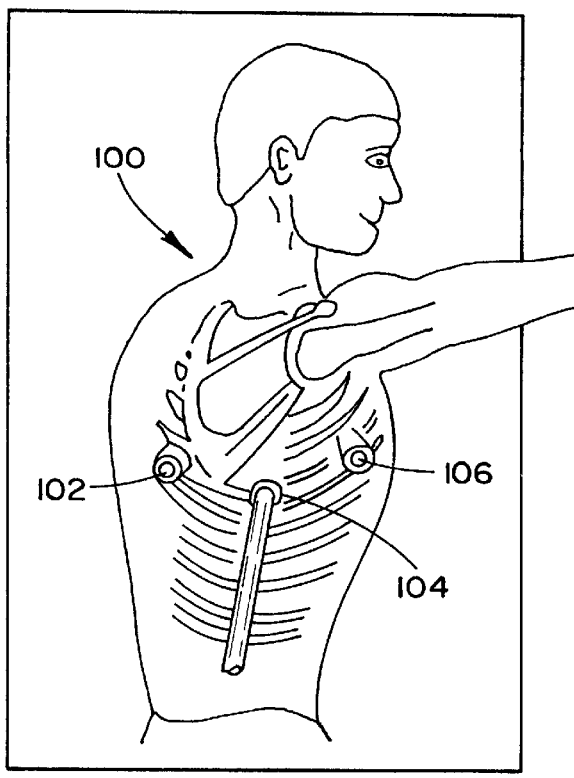
FIG. 1
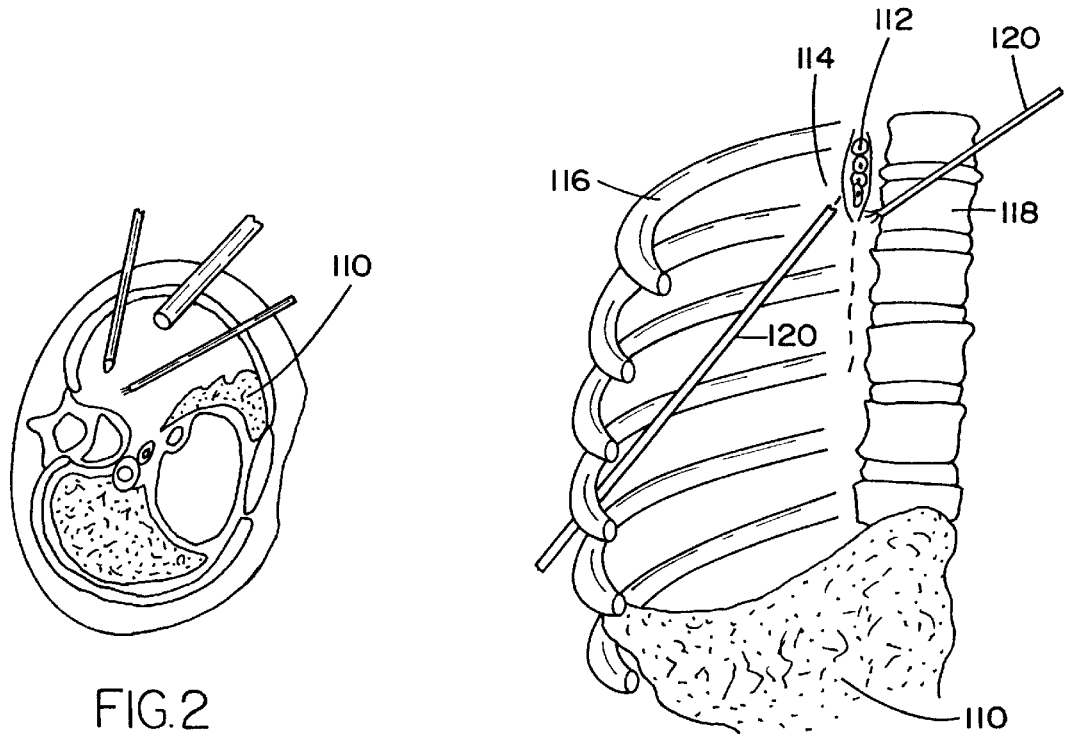
FIG. 2
FIG. 3

METHOD OF TREATING COMPLEX REGIONAL PAIN SYNDROMES BY ELECTRICAL STIMULATION OF THE SYMPATHETIC NERVE CHAIN

BACKGROUND OF THE INVENTION

1. Field of the Invention

This invention relates generally to the treatment of a group of physiological disorders known as complex regional pain syndrome, which is a multi-system, multi-symptom, syndrome usually affecting one or more extremities (but can affect any other part of the body) by the electrical stimulation of the corresponding cluster of nerves and/or ganglia in the sympathetic chain, adjacent to the corresponding vertebrae.

2. Description of the Prior Art

Within the field of neurosurgery, the use of electrical stimulation for the treatment of pathologies, including such disorders as uncontrolled movement, such as Parkinson's disease and essential tremor, as well as chronic pain and eating disorders, has been widely discussed in the literature. It has been recognized that electrical stimulation holds significant advantages over alternative methods of treatment, for example lesioning, inasmuch as successful lesioning destroys all nerve activity. Collateral damage to non-targeted tissues is also a significant risk in lesioning treatments. In many instances, it is, therefore, the preferred effect is to stimulate or reversibly block nervous tissue. Electrical stimulation permits such stimulation of the target neural structures, and equally importantly, it does not require the destruction of the nervous tissue (it is a reversible process, which can literally be shut off or removed at will). In addition, stimulation parameters can be adjusted so that benefits are maximized, and side effects are minimized.

The particular application which the present invention is directed to, is the treatment of complex regional pain syndromes. Complex regional pain syndrome (CRPS) type I, commonly known as reflex sympathetic dystrophy syndrome, or RSDS, was described 25 years ago. Several synonyms have been commonly employed in describing parts or all of this syndrome, including Raynaud's syndrome, vasomotor instability, occupational digital thrombosis, arteriosclerotic obliterative disease, etc. CPRS Type II, on the other hand, also known as causalgia, is a regional pain syndrome that develops after injury to a peripheral nerve, as first described during the Civil War by Dr. W. Mitchell. Spontaneous pain develops in the territory of the affected nerve which may then spread beyond that region. Vasomotor abnormalities and focal edema may occur alone or in combination in both CRPS types I and II. These are a severely disabling group of illness with simultaneous involvement of nerve, skin, muscle, blood vessels, and bones. While there are many symptoms associated with CRPS, the only common denominator is pain. The pain usually appears in one or more extremities, and is described as chronic, burning, and constant in nature. A syndrome of total body pain due to CRPS has been described as well. The remainder of symptoms may or may not occur. These symptoms include swelling, limited motor function which may lead to atrophy or dystrophy, tremor, focal dystonia or spasm, skin changes such as atrophy, dryness, and scaling, as well as bony changes with joint tenderness and swelling. In addition, vasomotor instability consisting of Raynaud's phenomenon (e.g. color changes and pain in fingers when exposed to cold), vasoconstriction or dilatation leading to cold and warm extremities respectively, as well as increased sweating.

The cause of the condition is currently not well understood and is often unrecognized. A number of precipitating factors have been associated with CRPS including minor trauma, cerebral or spinal cord lesions, ischemic heart disease and/or myocardial infarction, and repetitive cumulative trauma, such as carpal tunnel syndrome. However, in many of the patients a definite precipitating event can not be identified. Duration of CRPS varies, in many cases the pain continues on for at least two years and in some cases, indefinitely. Some patients experience periods of remissions and exacerbations. Periods of remission may last for weeks, months or years. The mean age of onset is in the mid thirties and there is increasing evidence that the incidence of CRPS in adolescents and young adults is on the rise. In Germany alone, for example, the annual incidence of RSD is estimated at 15000 [Dertwinkel, 1998]. Both sexes are affected, but the incidence of the syndrome is higher in women. Nonsurgical treatment consists of medicinal therapy, physical therapy, various peripheral or sympathetic nerve blocks, transcutaneous electrical nerve stimulation, or surgical sympathectomy. Patient response to therapy directly correlates to early diagnosis and treatment. However, the overall response rate to treatment is poor with over 50% of patients having significant pain and/or disability years later.

Abnormalities of autonomic function are present in both CRPS types I and II. Autonomic dysfunction results in localized sweating and changes in blood flow that may result in temperature asymmetries between affected and unaffected limbs. The changes in blood flow and sweating may result from localized noradrenergic and cholinergic hypersensitivity. Each body area has a regional cluster of nerve cells extending along the outside of the spinal column, and forming the sympathetic nervous system.

For example, the sympathetic outflow to the upper extremity lies in the inferior portion of the stellate or cervicothoracic ganglion down to the third thoracic ganglion. Similarly for the lower extremity, the sympathetic outflow passes through the second through fourth sympathetic ganglia. In general terms, the sympathetic, along with the parasympathetic, nervous system is part of the autonomic, or vegetative, nervous system. The effects of the autonomic system are extensive, and range from the control of blood pressure, heart rate, sweat, and body heat, to blood glucose levels, sexual arousal, and digestion.

While there are a variety of different techniques and mechanisms which have been designed to focus the lesioning means directly onto the target nerve tissue, collateral damage is inevitable. Were it even possible to direct all lesioning energy onto the target nerve cluster, it is a significant drawback that other functioning of these nerves is lost, even when such functioning may not be pathological. In addition, there are several common side effects described in the medical literature, including an ipsilateral Horner's syndrome (drooping eyelid and smaller pupil), compensatory sweating (increased sweating in other areas), and gustatory sweating (sweating, particularly of the face, at the smell of certain foods). It is because of the development of these and other side effects, including the poor response of medical or surgical therapy especially after a delay in treatment, that thoracic or lumbar sympathectomy has not enjoyed a greater popularity among physicians.

These complications, however, can be minimized to a large extent, or possible eliminated, by the use of chronic electrical stimulation or continuous drug infusion. The reasons are many, and include the possibility of changing which contacts of a multipolar lead are stimulated to minimize stimulating the superior portion of the stellate ganglion which can lead to a Horner's syndrome, to adjusting the parameters such as frequency or pulse width to affect changes in compensatory and gustatory sweating, should they arise. In addition, parameters may be intermittently adjusted if, and when, clinical efficacy is worsening in order to maximize therapeutic benefit It is therefore the principle object of the present invention to provide a less destructive and fully reversible and adjustable method of treating complex regional pain syndromes by electrically or chemically stimulating/inhibiting the appropriate portion(s) of the sympathetic chain.

SUMMARY OF THE INVENTION

The preceding objects are provided in the present invention, which comprises new and novel methods of treating complex regional pain syndromes by implantation of stimulation electrodes at specific locations along the sympathetic chain. More particularly the present invention comprises a method of therapeutically treating upper or lower extremity CRPS Type I or II by surgically implanting an electrode adjacent to a predetermined site along the sympathetic chain on the affected side of the body, or if clinically indicated, bilaterally. For upper extremity reflex sympathetic dystrophy (CRPS Type I), for example, this involves the surgical implantation of a stimulating electrode over the inferior portion of the stellate ganglion, and over T2–4. The most commonly employed surgical approach is aided by video-assisted thoracoscopy, which involves the placement of 2–4 small incisions or ports in the chest wall, through which instruments may traverse en route to the lateral aspect of the vertebral bodies where the sympathic chain lies extrapleurally. The distal end of the lead can be secured to surrounding tissues and be placed either directly over the sympathetic chain or over the internal aspect of the parietal pleura. The proximal end of the lead can be passed out of the thoracic cavity via one of the neighboring surgical ports, and tunneled subcutaneously to an electrical signal source which, in turn, is operated to stimulate the predetermined treatment site over the sympathetic ganglia, such that the clinical effects of the pain disorder are reduced with minimal side effects.

Alternatively, a catheter with either end- or side-apertures placed over the ganglia of interest is connected in a similar fashion to a infusion pump. In addition, this embodiment is extended to include a combination electrical contact and drug delivery system, as well as a system which has the capacity to sense or record electrical or chemical activity in the region of interest.

BRIEF DESCRIPTION OF THE DRAWINGS

FIG. 1 is a schematic illustration of a patient lying in the lateral decubitus position having one visualization port in the fifth intercostal space at the mid-axillary line and two instrument ports at the fourth and fifth intercostal space at the anterior and posterior axillary lines, respectively;

FIG. 2 is an axial cross section view of the upper thoracic region including one visualization port and two instrument ports wherein the two instrument ports have disposed therethrough endoscopic instruments accessing the ipsilateral paravertebral region where the sympathetic chain lies;

FIG. 3 is an exposed view of the left hemithorax displaying one instrument tenting the parietal pleura while the second endoscopic instrument is incising the parietal pleura to expose the sympathetic chain.

DETAILED DESCRIPTION OF THE PREFERRED EMBODIMENT

Figure 4:
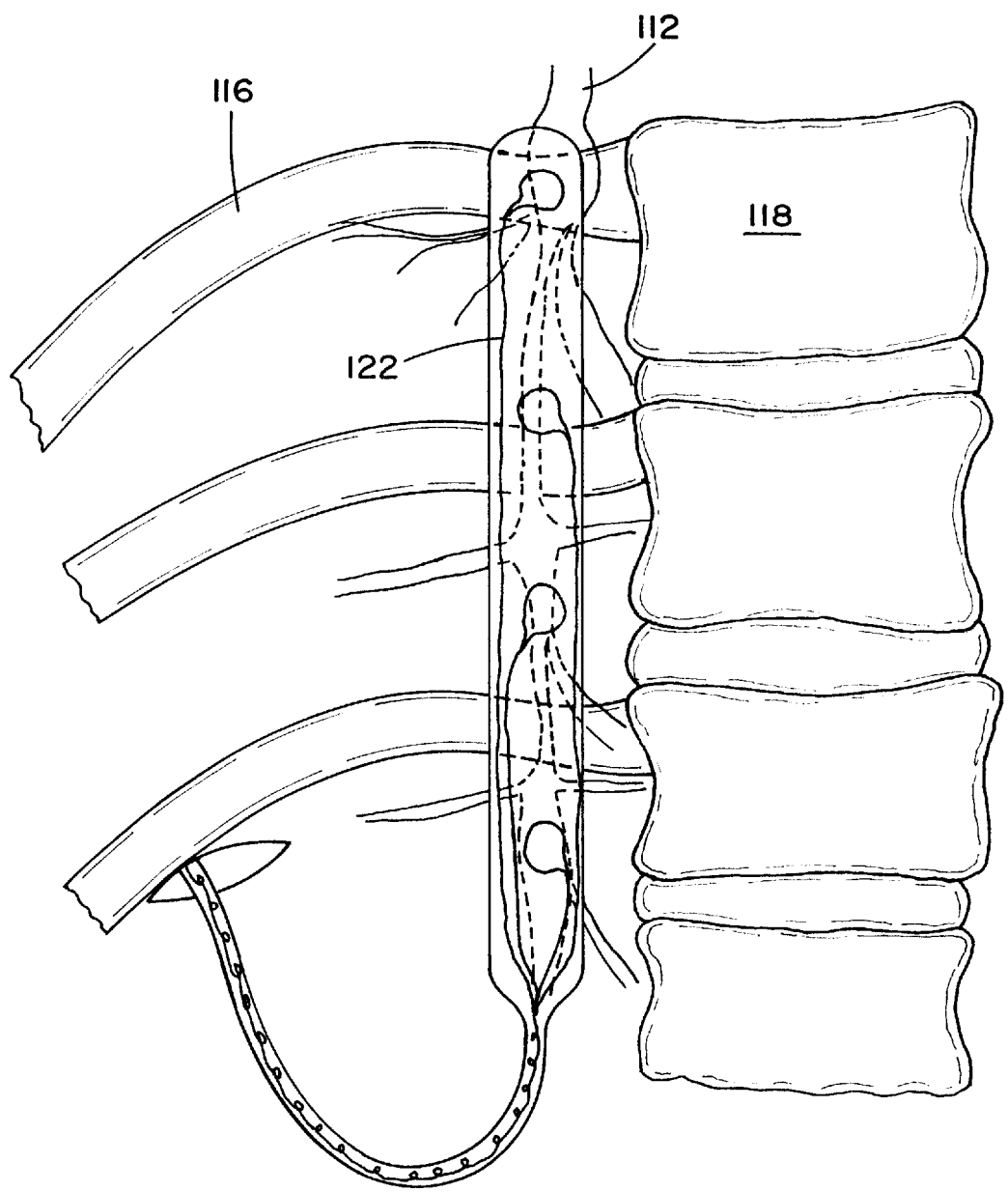
FIG. 4 is a side view of an exposed superior thoracic ganglia in which an electrical stimulation lead is disposed adjacent thereto.

There are many several approaches described in the literature that have been employed in the lesioning of the stellate and superior thoracic sympathetic ganglia, as well as other ganglion groups, such as the second through fourth lumbar sympathetic ganglia. With respect to this embodiment, any one or a combination of these methods, as well as modifications of this technique not herein described, may be possible without deviating from the broad spirit and principle of the present invention. Specifically, it will be apparent to those skilled in the art that variations and modifications are possible without deviating the scope of the current embodiment which describes the technique of changing the functional state of the upper thoracic and cervicothoracic (stellate) sympathetic ganglia or lumbar sympathetic ganglia via chronic electrical stimulation or infusion of drug known to modulate its function.

Referring now to FIG. 1, in which a patient 100 is illustrated in the decubitus position, having been prepared by the surgical insertion of three ports 102,104,106 into the left hemithorax. This preparation is anticipation of a thoracoscopic approach, which is a typical and feasible surgical technique utilized for lesioning of these ganglia. More specifically, this approach commonly involves positioning the patient in the lateral decubitus position, with the hips below the flexion joint of the operating room table. Subsequent flexion of the table allows some separation of the ribs by dropping the patient's hips and therefore increasing the intercostal space to work through. The ipsilateral arm is abducted on an arm holder. Rotating the table somewhat anteriorly and using reverse Trendelenburg positioning further maximizes the exposure to the superior paravertebral area by allowing the deflated lung (see FIGS. 2 and 3) to fall away from the apical posterior chest wall. The patient is under placed under general anesthesia and intubated via a double lumen endotracheal tube. This allows for ventilation of one lung, and collapse of the lung on the side to be operated upon without using carbon dioxide insufflation. Three 2 cm incisions for the thoracoscopic sympathectomy are ordinarily used. One incision is in the midaxillary line in the fifth intercostal space and is used as the telescopic video port 104. The second incision, performed under endoscopic observation, is placed in the third or fourth intercostal space at the anterior axillary line and is used as one of two instrument channels 106. The third incision is made at the posterior axillary line just below the scapular tip in the fifth interspace, and it is used as the second instrument channels 102. Additional incisions/ports can be made as necessary.

Referring now also to FIGS. 2 and 3, in which axial cross section and exposed views of the surgical field are provided, respectively, the surgical exposure and preparation of the relevant portion of the sympathetic chain for the treatment of hyperhidrosis is described. After the lung 110 is collapsed, and if necessary, retracted down by a fanning instrument via one of the working ports, the sympathetic chain 112 is visualized under the parietal pleura 114 as a raised longitudinal structure located at the junction of the ribs 116 and the vertebral bodies 118. The parietal pleura 114 is grasped between the first and second ribs in the region overlying the sympathetic chain 112 and the endoscopic cautery or scissors 120 is used to incise the pleura 114 in a vertical manner just below the first rib thereby exposing the sympathetic chain 112.

Referring now also to FIG. 4, in which the placement of the multichannel electrode adjacent to the symnpathetic chain is shown, the implantation of the stimulation electrode is now described. Once the sympathetic chain 112 has been exposed, a multipolar electrode 122 is placed over sympathetic chain of interest, typically the inferior third of the stellate ganglion to the T3 ganglion, and sutured in place to the nearby tissue or parietal pleura 114.

Alternatively one may prefer not to incise the parietal pleura 114 if electrical stimulation is used, as the current which is generated may modulate the functioning of the ganglia through the pleural surface. Pending the preference and comfort level of the surgeon, a temperature probe may be placed on the ipsilateral arm, and electrical stimulation (or in the case of the alternate drug infusion embodiment) testing may be performed prior to closure of the chest cavity to maximize the probability of future effective therapy.

This procedure can most easily be accomplished by using existing electrode configurations, or modifications thereof, with the distal tip being more superior, and the proximal tip and the connection cable being more inferior. The lead can be inserted into the thoracic cavity and held in place via the posterior axillary line incision and sutured by using the other working port. The proximal connecting cable can be left at the posterior axillary line port after the lead has been secured with some remaining 'slack of connecting cable being left in the inter-pleural space. The proximal end of the connecting cable/tube can be brought out of the thoracic cavity, and via an extension cable/tube, be tunneled subcutaneously and connected to an electrical pulse generator or infusing pump. The pulse generator or pump may be placed in the subcutaneous tissues of the flank area, abdominal wall area, or buttock area, etc. Any excess fluid is suctioned from the thoracic cavity and the lung is reinflated. A suctioning chest tube may or may not be used depending on the presence or absence of damage to the visceral pleura of the lung. The incisions are closed, and a chest X-Ray is obtained in the recovery room to ensure the lung has reinflated. Electrical stimulation or drug infusion therapy may be started immediately, or after a delay, allowing for some healing to occur first.

Alternative approaches include posterior open extrapleural techniques, posterior percutaneous approaches, the anterior supraclavicular method, as well as the open transthoracic approach. For the lower extremities, an open or videoscopically-assisted transabdominal approaches are most viable. Alternatively, posterior or modified percutaneous approaches are feasible. However, while there has been described and illustrated specific embodiments of new and novel methods of treatment for complex regional pain disorders, and it will be apparent to those skilled in the art that variations and modifications are possible, such alterations shall be understood to be within the broad spirit and principle of the present invention which shall be limited solely by the scope of the claims appended hereto.

We claim:

1. A method of interventionally and reversibly treating complex regional pain syndromes comprising:

implanting at least one electrode, having distal and proximal termini, such that the distal terminus is in the vicinity of the sympathetic chain;

coupling the proximal terminus of the at least one electrode to an electrical signal source;

applying an oscillating electric field to the sympathetic chain in a frequency range of 2 to 2500 Hz;

varying the frequency of the oscillating electric field until the symptoms of the pain syndrome have been demonstrably alleviated; and continuing the application of the oscillating electric field.

2. The method as set forth in claim 1, wherein the vicinity of the sympathetic chain is adjacent to the stellate ganglion.

3. The method as set forth in claim 1, wherein said stimulation increases nerve activity.

4. The method as set forth in claim 1, wherein said stimulation decreases nerve activity.

5. The method as set forth in claim 1, wherein said step of applying said oscillating electric field comprises applying said oscillating electric field in a high frequency range of 50 to 2500 Hz.

6. The method as set forth in claim 1, wherein said step of applying said oscillating electric field comprises applying said oscillating electric field in a low frequency range of 2 to 100 Hz.

7. The method as set forth in claim 1, wherein the at least one electrode is a monopolar electrode and the application of the oscillating electric field is monopolar.

8. The method as set forth in claim 1, wherein the at least one electrode is a bipolar electrode and the application of the oscillating electric field is bipolar.

9. The method as set forth in claim 1, wherein the at least one electrode is a multipolar electrode and the application of the oscillating electric field is multipolar.

10. The method as set forth in claim 1, wherein said step of applying said oscillating electric field comprises the step of operating said electrical signal source with a pulse width of selected from the range of 50 to 500 microseconds.

11. The method as set forth in claim 1, wherein said step of applying said oscillating electric field comprises the step of operating said electrical signal source with a voltage selected from the range of 0.1 to 20 volts.

* * * * *